US012563166B2

(12) United States Patent
Bourbon et al.

(10) Patent No.: US 12,563,166 B2
(45) Date of Patent: Feb. 24, 2026

(54) IMAGING METHOD FOR SEPARATING SPECTRAL SIGNAL COMPONENTS, AND ASSOCIATED ENDOSCOPY SYSTEM

(71) Applicant: Schölly Fiberoptic GmbH, Denzlingen (DE)

(72) Inventors: Johannes Bourbon, Freiburg (DE); Herbert Bohusch, Winden (DE); Stefan Schröer, Freiburg (DE); Matthias Kühn, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 715 days.

(21) Appl. No.: 17/869,877

(22) Filed: Jul. 21, 2022

(65) Prior Publication Data

US 2023/0028674 A1     Jan. 26, 2023

(30) Foreign Application Priority Data

Jul. 22, 2021    (DE) .......................... 102021119061.4

(51) Int. Cl.
   H04N 9/64       (2023.01)
   H04N 23/84      (2023.01)
            (Continued)

(52) U.S. Cl.
   CPC .............. H04N 9/64 (2013.01); H04N 23/84 (2023.01); *A61B 1/000095* (2022.02); *A61B 1/043* (2013.01)

(58) Field of Classification Search
   CPC .... H04N 9/64; H04N 23/84; A61B 1/000095; A61B 1/043

(Continued)

(56) References Cited

U.S. PATENT DOCUMENTS

| | | | | |
|---|---|---|---|---|
| 2013/0027591 A1* | 1/2013 | Lukac | ................. | H10F 39/8057 |
| | | | | 348/242 |
| 2024/0225432 A9* | 7/2024 | Segawa | ................ | A61B 1/0655 |

FOREIGN PATENT DOCUMENTS

WO      WO-2017042980 A1 *   3/2017

OTHER PUBLICATIONS

Egly, Dominik, et al. "A compact multi-channel fluorescence sensor with ambient light suppression." Measurement Science and Technology 23.3 (2012): 035702. (Year: 2012).*

(Continued)

*Primary Examiner* — Jonathan S Lee
(74) *Attorney, Agent, or Firm* — Volpe Koenig

(57) ABSTRACT

For simplified, less computationally intensive, image recording of different spectral signal components using a plurality of color channels of a single image sensor, a targeted adjustment of a sensitivity of at least one of the color channels in relation to another one of the color channels of the image sensor is provided for a spectral separation of this reduced or adjusted color channel from the other color channel so that at least one certain spectral range (i.e., in particular a part of a first spectral range captured using the other color channel) is no longer detectable using the color channel that has been adjusted in terms of its sensitivity. This adjusted color channel becomes spectrally blind in the spectral range and can consequently spectrally selectively detect a further spectral range (specifically a second spectral range deviating from the first spectral range). The second spectral range may include a fluorescence wavelength.

20 Claims, 2 Drawing Sheets

(51) Int. Cl.
    *A61B 1/00*        (2006.01)
    *A61B 1/04*        (2006.01)
(58) Field of Classification Search
    USPC ........................................................ 382/167
    See application file for complete search history.

(56)                References Cited

OTHER PUBLICATIONS

Li, Jia, et al. "Optimized color filter arrays for sparse representation-based demosaicking." IEEE transactions on image processing 26.5 (2017): 2381-2393. (Year: 2017).*

* cited by examiner

IMAGING METHOD FOR SEPARATING SPECTRAL SIGNAL COMPONENTS, AND ASSOCIATED ENDOSCOPY SYSTEM

INCORPORATION BY REFERENCE

The following documents are incorporated herein by reference as if fully set forth: German Patent Application No. 10 2021 119 061.4, filed Jul. 22, 2021.

TECHNICAL FIELD

The invention relates to an imaging method, in particular for medical applications such as video endoscopy for example, wherein a scene is illuminated by illumination light in a first spectral range and the illumination light is recorded by a main color channel of an image sensor. In this case, the image sensor has at least one further color channel.

The invention further relates to an associated endoscopy system which comprises an image sensor embodied as a single chip, said image sensor having at least two color channels which are formed by means of a color filter array (CFA), and a light source. This light source, which may be formed from a plurality of light sources in particular, serves to produce illumination light within a first spectral range of the visible spectrum and to produce excitation light for exciting an emission of fluorescence light, the fluorescence light lying in a second spectral range which lies just outside of the first spectral range.

BACKGROUND

By way of example, the prior art has disclosed many different methods that can be used to record fluorescence light with the aid of an endoscope and to represent said fluorescence light, for example in the form of an image overlay in a color image likewise recorded by the endoscope. Typically, color sensors with a color filter array (CFA) are used to this end. Frequently, the signals of individual color pixels are combined by calculation since the sensitivity of all pixels is typically equal in the infrared (IR) range for example and hence an IR image, that is to say an image which represents the respective spectral signal component produced by IR radiation, can be calculated from all color pixels by way of an appropriate combination of the signal components by calculation. By combining the signals of individual pixels by calculation, spectral signal components produced not by the IR fluorescence light in the infrared range but for example by illumination light in the visible range (VIS=visible wavelength) are removed by calculation in the process. That is to say these VIS signal components are spectrally separated from the desired IR image by the signal processing.

SUMMARY

Proceeding from this technical background, the invention is based on the object of finding a technical alternative to such previously known methods which are computationally intensive in particular. This should achieve a lower energy consumption or a simplified imaging method. By way of example, the method should allow signal components caused by fluorescence light to be separated from signal components produced by visible light in order to thus facilitate "enhanced imaging", that is to say imaging with an enhanced functionality.

To achieve this object, one or more features according to the disclosure are provided in an imaging method. In particular, for the purposes of achieving the object, the invention thus proposes that, in an imaging method of the type set forth at the outset, the sensitivity of at least one "reduced color channel" of the at least one further color channel is selectively reduced in comparison with a sensitivity of the main color channel to such an extent that the illumination light, in particular in the first spectral range, still is capturable using the reduced color channel but is no longer measurable and/or that said illumination light produces a negligibly small signal component.

The decisive advantage of this method lies in the fact that the reduced color channel (following the reduction in its sensitivity) is no longer interfered with by spectral components of the illumination light, and so a spectral separation is obtained between the reduced color channel and the illumination light used for imaging. As a result, the reduced color channel is able to detect light spectrally selectively in a second spectral range lying outside of the first spectral range of the illumination light, for example detect a certain fluorescence wavelength. Consequently, it is possible to dispense with a spectral signal separation by means of computationally intensive and hence energy intensive signal processing. This is because the output signal of the color channel can in particular be designed by the reduction in sensitivity such that it no longer correlates with the spectral signal components of the first spectrum/the illumination light, that is to say it is no longer influenceable by the illumination light. Therefore, such signal components no longer need to be removed from the output signal of the reduced color channel by calculation either, as was the case in the previously known methods (in which the output signals of a plurality of color channels were correlated with one another since these detect overlapping spectral ranges).

To this end, the invention in particular proposes to reduce the sensitivity of the reduced color channel on the basis of a spectral intensity distribution of the illumination light. Consequently, the exact spectrum of the utilized illumination light source should be known, or should be determined in advance, in order to facilitate a suitable (minimal) reduction in the sensitivity.

Further, it is preferable for a simple implementation of the method if the sensitivity is reduced to the same extent for all wavelengths that are detectable using the reduced color channel. For instance, this can be implemented by a (global) adjustment of a threshold correction, as will still be explained in more detail below.

In this case, the reduction in sensitivity can in particular be implemented dynamically, that is to say in time varying fashion. For instance, if the intensity of the illumination light increases (which is indirectly detectable from a control of the responsible illumination source), in particular in a spectral overlap range of the color channels, it is possible to reduce the sensitivity of the at least one color channel to a greater extent. That is to say, the reduction can also be adjusted during the image recording on the basis of further parameters, in particular an illumination and/or excitation light intensity used during the recording.

If a plurality of further color channels are used, the sensitivities thereof can be reduced individually and independently of one another, in particular on the basis of a currently used illumination spectrum.

Further, for example, at least one of the further color channels can also be used as a further main color channel in order to measure the illumination light—in addition to the main color channel—therewith.

In the case of a standard RGB Bayer sensor as a possible sensor type with which the method according to the invention is realizable, the blue and the green color channel can for example each act as main color channel in order to detect illumination light in the blue to green visible wavelength range while the red color channel can be used as reduced color channel for detecting fluorescence light, in particular in the NIR wavelength range. As a result of reducing the sensitivity of the red color channel in this specific exemplary embodiment, the red color channel becomes insensitive to the green and blue visible illumination light and so fluorescence light imaging with the reduced red color channel can be implemented without being impeded by the two spectra of the illumination light.

According to the invention, the object can also be achieved by further advantageous embodiments as described below and in the claims.

For instance, provision can be made for at least one fluorescent dye to be excited by means of excitation light to emit fluorescence light, and for both the illumination light and the fluorescence light to be measured or recorded by means of the image sensor. In this case, it is preferable for the image sensor to be embodied as a single chip. In this case, the fluorescence light can preferably be measured using the at least one reduced color channel.

Thus, provision can be made for the at least one reduced color channel to be used for fluorescence light imaging while the main color channel is simultaneously used for VIS imaging, that is to say for imaging in the visible wavelength range (visible wavelengths=VIS).

What can be achieved by reducing the sensitivity of the reduced color channel is that the illumination light used for VIS imaging is no longer measurable using the reduced color channel and/or produces a negligibly small signal component. Additionally, the sensitivity of the main color channel, which is provided for VIS imaging, may also be reduced so far in the process that the main color channel becomes insensitive to the wavelengths of the fluorescence light. That is to say the fluorescence light is no longer measurable using the main color channel and/or produces a negligibly small signal component in the main color channel.

By contrast, if the color channel used for the fluorescence light imaging is insensitive to VIS wavelengths in any case (for instance if an NIR color channel is used), it is also equivalently possible to only reduce the sensitivity of the color channel used for VIS imaging (such that the latter then forms the "reduced color channel" within the meaning of the invention). In such a case, too, the VIS imaging can be carried out in a manner unimpeded by the fluorescence light and the fluorescence light imaging can be carried out in a manner unimpeded by the VIS illumination light.

As a rule, the excitation light used for the fluorescence light imaging will lie in a spectrum which at least partly deviates from the spectrum of the illumination light. This means that the excitation light contains wavelengths not contained in the illumination light (and vice versa). However, there may also be a partial spectral overlap between the excitation light and the illumination light in this case. By way of example, the excitation light can be kept away from the image sensor with the aid of a notch filter.

By way of example, if use is made of two different fluorescent dyes that emit different fluorescence light wavelengths, these fluorescence light wavelengths can each be detected using at least two reduced color channels. In this case, the signal components of the two fluorescence light wavelengths—taking account of the respective spectral sensitivities of the two reduced color channels—can be separated from output signals of the two reduced color channels by processing or combining by calculation.

What may arise in many application situations is that prior to the sensitivity reduction, respective spectral sensitivities of the main color channel and of the reduced color channel overlap in at least one spectral overlap range, in which the respective sensitivities are above an omnispectral sensitivity threshold. In this case, reducing the sensitivity of a color channel is tantamount to increasing the associated intensity threshold above which a signal at a certain wavelength is just still measurable using the color channel (wherein such thresholds can for example be ascertained using a light source for a certain image sensor, said light source being tunable in terms of spectrum and intensity). In this case, a particularly sensitive color channel will also still be able to measure very small intensity values at a certain wavelength (consequently of a low intensity threshold), while a color channel reduced in its sensitivity is just no longer able to measure such values at this wavelength (on account of an increase in the intensity threshold). This means that an overlap between two color channels (within the meaning of the invention) at a certain wavelength exists precisely when both color channels exhibit a sensitivity above the sensitivity threshold for this wavelength. That is to say, both color channels can measure (depending on the wavelength only just still) the associated intensity threshold in the spectral overlap range.

In this case, the term "omnispectral" can be understood to mean "equal for all wavelengths" or "omnifrequent". This means that the image sensor is able to measure intensities above the omnispectral sensitivity threshold, independently of the wavelength, that is to say for all wavelengths relevant to the imaging.

Consequently, in the above-described situation, prior to the sensitivity reduction, spectral signal components in the at least one overlap range which are above an associated omnispectral intensity threshold can be measurable using the main color channel and the reduced color channel. By contrast, following the reduction in the sensitivity of the reduced color channel, the latter's reduced sensitivity in at least one spectral separation range can then lie below the omnispectral sensitivity threshold. This is advantageous in that in the separation range the at least one reduced color channel then no longer measures light from the first spectral range below the omnispectral intensity threshold.

In this case, it should be taken into account that the intensity threshold corresponds to an intensity that has been integrated/added over a certain wavelength spectrum. This is because the pixels of the image sensor integrate over a plurality of wavelengths.

What can consequently be achieved comparatively easily using the above-described method is that spectral signal components which are detectable as a matter of principle by means of the at least two color channels of the image sensor (for example in the second mode explained in more detail below) can be separated from one another, in particular in intensity-dependent fashion.

What can further be achieved by reducing the sensitivity of the at least one color channel is that the illumination light, in particular in the visible wavelength range, is no longer measurable below an intensity threshold, in particular the intensity threshold, using the at least one reduced color channel. Expressed differently, the illumination light, in particular below the intensity threshold, can consequently still be measurable further using the main color channel.

The at least one overlap region described above may for example lie within a first spectral range of the visible spectrum. In this case, the at least one reduced color channel, despite, i.e., following, the sensitivity reduction, can continue to remain sensitive to spectral signal components above the intensity threshold in a second spectral range lying outside of the first spectral range. Therefore, this second spectral range can be used for fluorescence light imaging, for example.

It is understood that it is preferable in this case for an optimal spectral separation if the reduced color channel is no longer sensitive to spectral signal components below the intensity threshold below or above a limit wavelength (e.g., in the visible spectrum). Accordingly, this last feature describes a state in which wavelengths lying below or above the limit wavelength (in particular in the visible spectrum) are no longer measurable using the reduced color channel. Therefore, these wavelengths no longer interfere with the reduced color channel and can for example be used as illumination light, for instance if the reduced color channel detects fluorescence light in the IR range. This means that the reduced color channel, more precisely its spectral filter characteristic, can be chosen precisely such that the desired insensitivity of the reduced color channel to the illumination light is obtained after an (in particular omnispectral) reduction in its sensitivity. At the same time, a high spectral sensitivity (even after the reduction) can further remain ensured in a second spectral range, for example in the IR range.

What can happen as a result of the sensitivity being reduced is that a dynamic range of the at least one reduced color channel is reduced. This reduction may occur in particular in comparison with a dynamic range prior to the sensitivity reduction and/or with a dynamic range of the main color channel. Therefore, in such cases the dynamic range can be retrospectively stretched to an original dynamic range or can be adapted to a deviating dynamic range following the recording of an image component (in particular a fluorescence light image component) using the at least one reduced color channel. By way of example, a tone mapping method can be used to adapt the original dynamic range to the dynamic range of utilized display equipment (in particular in the case of an HDR representation).

According to a further embodiment, provision can be made for the sensitivity of the at least one reduced color channel in a first imaging mode, in which the at least one reduced color channel is used for the fluorescence light imaging, to be reduced in comparison with its sensitivity in a second imaging mode, in which the reduced color channel is used as non-reduced main color channel for imaging in the visible wavelength range. This means that one and the same color channel can be used in one case as a reduced color channel and in another case as a non-reduced color channel depending on the mode.

In this case, provision can also be made for a white-light illumination used for imaging to be automatically adapted to a reduced white-light illumination as soon as there is the change between these two imaging modes. By way of example, this reduced white-light illumination can be distinguished in that it has a reduced spectrum in comparison with the previously used white-light illumination and/or an intensity that is reduced in certain spectral ranges. In this case, it is naturally expedient to precisely omit the wavelengths which lie close to or within an original overlap range of the color channels, or at least reduce said wavelengths in terms of the intensity (for instance, by way of appropriate spectral filters). This is because this can prevent the reduced color channel from being disturbed by these wavelengths of the white-light illumination. Wavelengths for which the reduced color channel is not sensitive in any case, by contrast, can continue to be used for illumination purposes without change, even in the reduced white-light illumination.

The change between these two imaging modes can also be implemented automatically as soon as a user adjusts a white-light illumination used during the imaging to a reduced white-light illumination.

A further variant of the method provides for the reduction in the sensitivity of the at least one reduced color channel to be implemented pixel-by-pixel. By way of example, this means that only those pixels of the image sensor which belong to the at least one reduced color channel are used for measuring fluorescence light. In particular, the parallel detection of the fluorescence light by means of the main color channel can be ignored in this case.

Further, provision can also be made for the reduction in the sensitivity of the at least one reduced color channel to be independent of a utilized sensitivity of the main color channel. This is because such reductions in the sensitivity of the reduced color channel can be implemented, in particular, by means of an increase in an associated threshold correction, in particular a black level correction. In particular, this can be carried out on a pixel-by-pixel basis.

If the method for fluorescence light imaging is used, a fluorescence light image component (FLBK) used to visualize recorded fluorescence light can be calculated or derived exclusively from output signals of the at least one reduced color channel. It is also conceivable that, for example, a first fluorescence light image component (FLBK1) and a second fluorescence light image component (FLBK2) are respectively calculated or derived from output signals of at least two reduced color channels. In this case, each of these channels can be reduced individually in terms of its sensitivity. This indeed means that a certain amount of signal processing may also occur in this case. However, the spectral separation of the color channels continues to be carried out on the basis of the sensitivity reduction and not on the basis of removing spectral signal correlations, that is to say different spectral signal components, by calculation. Hence, both of the reduced color channels, in particular, can each be spectrally separated from the main color channel and can also be spectrally separated from one another.

Reducing the sensitivity of the at least one reduced color channel can be implemented in a wide variety of ways. By way of example, the sensitivity of the at least one reduced color channel can be reduced by virtue of, for the at least one reduced color channel (i.e., in particular also on an individual basis for individual reduced color channels):

i) a threshold correction being increased; and/or ii) an electronic exposure time, in particular for individual pixels, being continuously and/or alternately reduced in comparison with an electronic exposure time used for the main color channel; and/or iii) the individual color channels of the image sensor being read sequentially and an optical exposure time being adapted continuously and/or alternately such that the at least one reduced color channel is optically exposed for a shorter time period than the main color channel.

These three basic options can also be combined with one another as desired.

In particular, option ii) can be designed in such a way that different exposure times are realized for different pixels.

By contrast, provision can be made in option iii) for the sensitivity to be precisely not reduced for at least one main color channel, in particular the main color channel.

A threshold value correction according to option i) can be understood to mean that, in particular, a certain signal threshold, for example a signal threshold defined in advance, is subtracted from signals of the image sensor (within the affected color channel). By way of example, what can be achieved thereby is that the image sensor outputs a zero signal for actual measurement signals at a certain wavelength that are below the signal threshold. This means that the relevant color channel then is no longer sensitive below an associated intensity threshold which precisely produces said signal threshold. By way of example, such a procedure is applied in the case of a black level correction such that the threshold value correction can be a black level correction in particular.

By way of example, the electronic exposure time can be adjusted by adjusting the image processing chain or by adjusting an electronic shutter (as is conventional in the case of CMOS image sensors). By contrast, the sensitivity can be altered by adjusting a gain.

By way of example, the optical exposure time can be set by adjusting an optomechanical shutter used for imaging. Moreover, current image sensors in part already permit a line-by-line or column-by-column change in the exposure time and/or a frame-dependent change in the exposure time. The latter can also be adjusted in this way.

According to a further variant, the sensitivity of the at least one reduced color channel and a sensitivity of the main color channel can also be reduced and increased dynamically, in particular globally and together. In this case, the at least one reduced color channel and the main color channel can then be read at different times in order thus to achieve the desired spectral separation. This is because in that case the reduced color channel can be read precisely when the sensitivity is globally reduced while the main color channel can be read at a time when the sensitivity reaches a maximum.

Accordingly, this allows the first spectral range to be measured by means of the main color channel with a non-reduced sensitivity and a second spectral range to be measured by means of the at least one reduced color channel with a reduced sensitivity, the measurements being carried out at different times. This variant consequently represents a possible implementation of the method according to the invention; however, it is preferable for the sensitivities of the color channels of the image sensor to be reduced independently of one another, in particular at different times. By way of example, the adjustment of the sensitivity at different times can be carried out column-by-column or row-by-row or individually for individual pixels of the image sensor.

A further variant of the method therefore proposes that a sensitivity of individual pixels of the at least one reduced color channel is reduced differently pixel-by-pixel and/or to a different extent at different image recording times.

Following this approach, the reduction in sensitivity can consequently be implemented with a local variation in relation to a sensor surface of the image sensor and/or with a variation over time in relation to different exposure times of individual pixels of the image sensor. This can preferably be implemented using a reduction function Reduce(t,x,y), which changes over a sensor surface A(x,y) of the image sensor and/or changes over time. By way of example, a convergence of the different illumination of fluorescence excitation light and white light can be achieved by such method features since the excitation light as a rule will have a smaller illumination field than the illumination light. Further, this can also achieve a convergence of measurement values from the edge to the center of the image sensor and/or a compensation of an elevated excitation in the center (for instance if the excitation light source has an intensity maximum which is imaged on the center of the image sensor). Finally, such features can also be used to achieve a convergence of measurement signals in order thus to compensate effects arising as a result of the utilized imaging optical unit. By way of example, conventional optical units often exhibit a brightness distribution that is high in the center of the image and drops after the image edge; this is known as vignetting.

As explained above, a first image component can be recorded in a first spectral range, in particular the first spectral range, of the visible spectrum using the main color channel. In particular, this can be implemented using an illumination in a portion of the visible spectrum, in particular in the first spectral range. That is to say, a reduced VIS illumination, in particular, can be used to this end, for example by using a color filter on a white-light source.

In this case, the at least one reduced color channel can be used simultaneously to record a second image component in a second spectral range, in particular the second spectral range, which lies outside of the first spectral range. This can be implemented using (separate) excitation light for producing fluorescence light.

Consequently, the first image component preferably is a polychromatic image component which is recorded using at least two main color channels of the image sensor, for example using a green and a blue color channel.

By contrast, the second image component can be a monochromatic image component which is recorded using a reduced color channel; however, it may also likewise be a polychromatic image component determined using at least two reduced color channels.

As already mentioned, suitable filters can be used to prevent the excitation light from producing significant signal components on the image sensor, to be precise in relation to all color channels of the image sensor. This facilitates the described selective detection of the excitation light even in cases where the excitation wavelength is tightly adjacent to a recorded fluorescence wavelength.

In this case, a capture using only one color channel is also possible even if the fluorescence signal covers a relatively broad spectral range (e.g., 50 nm width). By way of example, when fluorescence light is observed in the NIR wavelength range, the observation of this light using a blue, red or green color channel is virtually equivalent since typical color filters converge in the NIR range in relation to their sensitivity/transmissivity, specifically when the color filters exhibit substantially the same transmission in the NIR such that then the sensitivity is predominantly determined by the utilized semiconductor materials of the image sensor.

The image sensor used in the method can moreover be usable or used in a second imaging mode, in which imaging is carried out in the visible wavelength range, in particular using a white-light illumination, using one of the color channels of the image sensor which is used in a first imaging mode, in particular the aforementioned first imaging mode, with one of the above-described methods as reduced color channel.

As mentioned, the sensitivity of the at least one reduced color channel can be reduced pixel-by-pixel for individual pixels of the image sensor. In particular, this can be implemented on the basis of a current intensity measurement value of a respective pixel. The respective pixel in this case can be the pixel whose sensitivity is currently intended to be reduced, or else some other pixel. This means that, firstly, the reduction carried out for a certain pixel of a reduced color channel may depend on the intensity value currently output by said pixel; secondly, the sensitivity reduction of certain pixels may also be carried out on the basis of intensity values of other pixels of the image sensor.

Conventional image sensors often already provide the option of reading temporally successive frames or else pixels in row-by-row and/or column-by-column fashion with a different dynamic range, for instance by a row-by-row adjustment of an electronic exposure time. This allows the intended pixel-by-pixel reduction in sensitivity to be realized particularly easily.

Further, what may also arise in certain recording situations is that the sensitivity of individual pixels of a reduced color channel is precisely not reduced while the other pixels of the reduced color channel are currently being reduced or are reduced.

It is understood that the sensitivity of a color channel of the image sensor available as a matter of principle, in particular an available dynamic range, may also be intermittently or permanently reduced in other imaging modes.

Finally, the reduction in the sensitivity of the at least one reduced color channel may also be implemented on the basis of numerous other parameters, such as for example:

a) an illumination light intensity currently used for imaging; and/or b) a current operation or imaging mode; and/or c) a current electronic gain or analog gain; and/or d) a utilized exposure time; and/or e) a currently used system component such as for example a certain light source, in particular a certain excitation light source, or an endoscope; and/or f) at least one secondary parameter such as for example i) values of a color matrix used to adjust a color representation and/or ii) values of a false color or heat map representation of images recorded using the method.

These options a) to f) can naturally also be combined as desired, for example depending on the available hardware.

A further imaging method, possibly with inherent inventive quality, is also proposed to achieve the object: Although this method may also be designed with features as described above, the method initially is distinguished by virtue of the fact that raw image data are recorded using at least two color channels of an image sensor and a signal threshold is subtracted from the raw image data in each case. Further, this method is specifically characterized in that a first set of signal thresholds (in particular of first black levels) is used in a first mode and a second set of signal thresholds (in particular of second black levels) is used in a second mode, to correct the respectively recorded raw image data. In particular, a difference and/or a quotient of the signal thresholds of the first set can be different from a difference and/or a quotient of the signal thresholds of the second set in this case. In this case, the two modes correspond to different imaging modes.

A spectral separation of at least one of the color channels of the color sensor is obtained by way of this second method according to the invention, in a manner equivalent to the first method according to the invention set forth at the outset, as a result of which all of the advantages set forth at the outset can be realized. By using a second adapted set of signal thresholds (which deviate from those of the first set and for example may be stored in an internal memory of an endoscope), the sensitivity of said color channel, in comparison with the sensitivity which this color channel has in the first mode, can be reduced in a targeted fashion in the second (imaging) mode. This method also realizes the inventive concept of obtaining a spectral separation not by signal processing but by selective adaptation of the sensitivity of (at least) one color channel of the image sensor. In this respect, this method also follows the general concept of the invention presented here.

In all methods presented until now, a scene (to be recorded) can be illuminated using an illumination light, in particular the illumination light, for an intended image recording. In this case, the threshold correction that is applied to a reduced color channel of the at least two color channels can be greater than the threshold correction applied to a main color channel of the image sensor. However, in this case, the reduced color channel may also have been less sensitive than the main color channel in relation to the illumination light, even before the threshold correction.

Moreover, an endoscopy system is proposed to achieve the object. This endoscopy system, which may be designed as explained at the outset, is precisely distinguished by virtue of the fact that the endoscopy system comprises an image processing unit which is configured to capture the fluorescence light of the light source (in particular exclusively) using at least one reduced color channel of the color channels of the image sensor. In this case, the sensitivity of this reduced color channel is thus reduced or has been reduced by the image processing unit, to be precise in comparison with the sensitivity of at least one main color channel of the color channels of the image sensor.

The described sensitivity reduction by the image processing unit can preferably be achieved by carrying out one of the imaging methods already explained above or in accordance with one of the claims directed to an imaging method. This means that the image processing unit can be precisely configured to carry out one of the above-described imaging methods or an imaging method in accordance with any one of the method claims.

The image processing unit can preferably also be configured to record the illumination light (at least in part) by means of the at least one main color channel. Moreover, the endoscopy system may naturally comprise the appropriate control means for casting illumination light and/or excitation light, depending on the image recording mode, onto the scene with the aid of the light source.

In this case, the two spectral ranges (i.e., the illumination light and the fluorescence light) may overlap in particular, that is to say the second spectral range can for example be a portion of the first spectral range.

Once again, the excitation light may also lie within the first spectral range, that is to say in particular within the visible spectral range, wherein the excitation light can then be filtered out or removed by calculation in any other way; by way of example, only a very small part of the visible spectrum needs to be subtracted in the case of filtering when a monochromatic light source is used for the excitation light, and so the filter used to this end need not have a substantial effect on the VIS imaging.

The image processing unit can consequently implement one of the above-described imaging methods automatically or independently without the user having to intervene in this respect (apart from switching between the imaging modes, and other settings which the user implements according to their preferences).

The image processing unit can consequently be configured to carry out the reduction in the sensitivity of the at least one reduced color channel on the basis of very different parameters or else adapt said reduction (dynamically during the image recording). By way of example, such parameters can be a system component currently used in the endoscopy system, that is to say the reduction/adaptation can be implemented for example on the basis of a light source currently used for imaging and/or an endoscope used to this end; and/or on the basis of a current operation or imaging mode, to name but a few examples.

Further, the endoscopy system may also comprise two image sensors, in particular in order to facilitate stereoscopic vision. In this case, a dedicated image processing unit can be provided for each of the two image sensors, the image processing unit being configured as described above.

BRIEF DESCRIPTION OF THE DRAWINGS

The invention will now be described in more detail on the basis of exemplary embodiments, but is not restricted to these exemplary embodiments. Further developments of the invention can be obtained from the following description of a preferred exemplary embodiment in conjunction with the general description, the claims and the drawings.

In detail.

DETAILED DESCRIPTION

Figure 1:
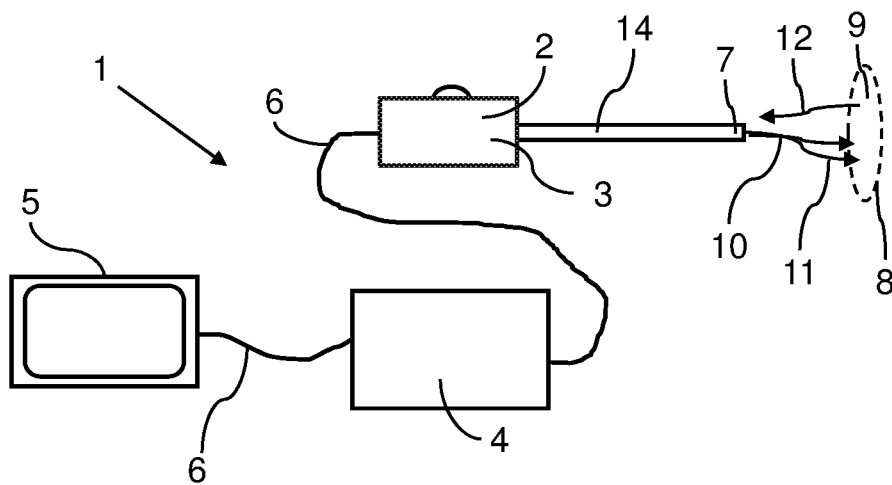
FIG. 1 shows a schematic view of an endoscopy system according to the invention.

FIG. 1 shows an endoscopy system 1 according to the invention, which comprises an endoscope 2, an associated camera control unit (CCU) 4 and a monitor 5. The endoscope 2 is designed as a chip-in-tip endoscope 2 since the image sensor 7 is mounted at the distal end of the shaft 14. Illumination light 10 is transported via light guides from an internal light source 3 of the endoscope 2 to the distal tip of the endoscope 2 in order thus to illuminate a tissue 8 that is observed by means of the endoscope 2.

The endoscopy system 1 can also be formed with the aid of an endoscope 2 (chip-in-scope). In yet another alternative, the image sensor(s) 7 is/are situated in a camera head which can be assembled with an endoscope 2 to form an imaging system.

To let these processes run in automated fashion, the camera control unit 4 comprises an image processing unit which takes over both the reading of the image sensor 7 and the control of the light sources. In the process, the CCU 4 in particular recognizes the imaging mode (see the explanations below) the user of the endoscope 2 currently has selected and accordingly chooses the required light source, or drives the latter. These light sources may for example also comprise filter wheels such that the CCU 4 can also adapt the spectrum of the illumination and/or excitation light 10, 11 in a targeted manner.

The illumination light 10 also contains wavelengths (in particular the wavelength of 810 nm) which, as excitation light 11, optically excite a fluorescent dye 9 (in this case indocyanine green (ICG)) in the tissue 8 so that the latter emits fluorescence light 12 which should precisely be recorded using the image sensor 7. To this end, the excitation light 11 can in particular be provided using a separate excitation light source, for example an LED that emits with a narrow bandwidth (using an additional passband filter) around 810 nm.

The image sensor 7 is embodied as a standard Bayer pattern RGB sensor based on only a single image sensor chip. The image sensor 7 consequently comprises red, green and blue pixels which are each formed by way of appropriate color filters (by way of example, quantum dot-based pixels would also be possible in an alternative), with the red, green and blue color filters being arranged in a Bayer pattern on the light-sensitive surface of the image sensor 7.

In this case, the totality of red color pixels, which each are able to detect luminous intensity values at different spatial positions on the image sensor 7, forms a first red color channel. Accordingly, the totality of blue pixels forms a blue color channel and the totality of green pixels forms a green color channel. In this case, the spectral sensitivity of the respective color channel precisely corresponds to the respective transmission curve of the respective pixel in combination with the sensitivity of the photocells located therebelow, which are depicted in FIG. 2.

Figure 2:
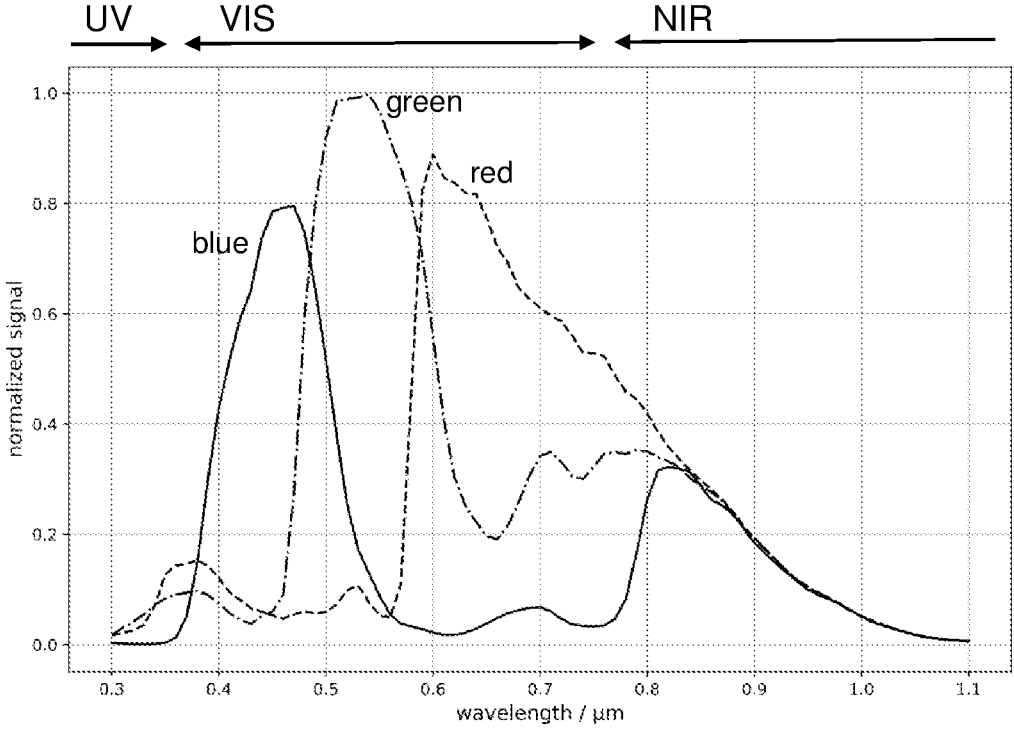
FIG. 2 shows transmission spectra of red, green and blue pixels of the image sensor of the endoscopy system of FIG. 1.

As is evident from FIG. 2, the transmission curves of the individual different pixels, and hence the sensitivity of the assigned color channels, converge in the infrared (IR) range since the color filters exhibit substantially the same transmission there and the sensitivity is therefore determined by the utilized semiconductor material of the image sensor 7.

The challenge now precisely consists of recording the very low intensity of the fluorescence light 12 at 830 nm (cf. FIG. 3) using the endoscope 2 while high intensities of the other illumination light 10 reflected by the tissue reach the image sensor 7 at the same time.

Figure 3:
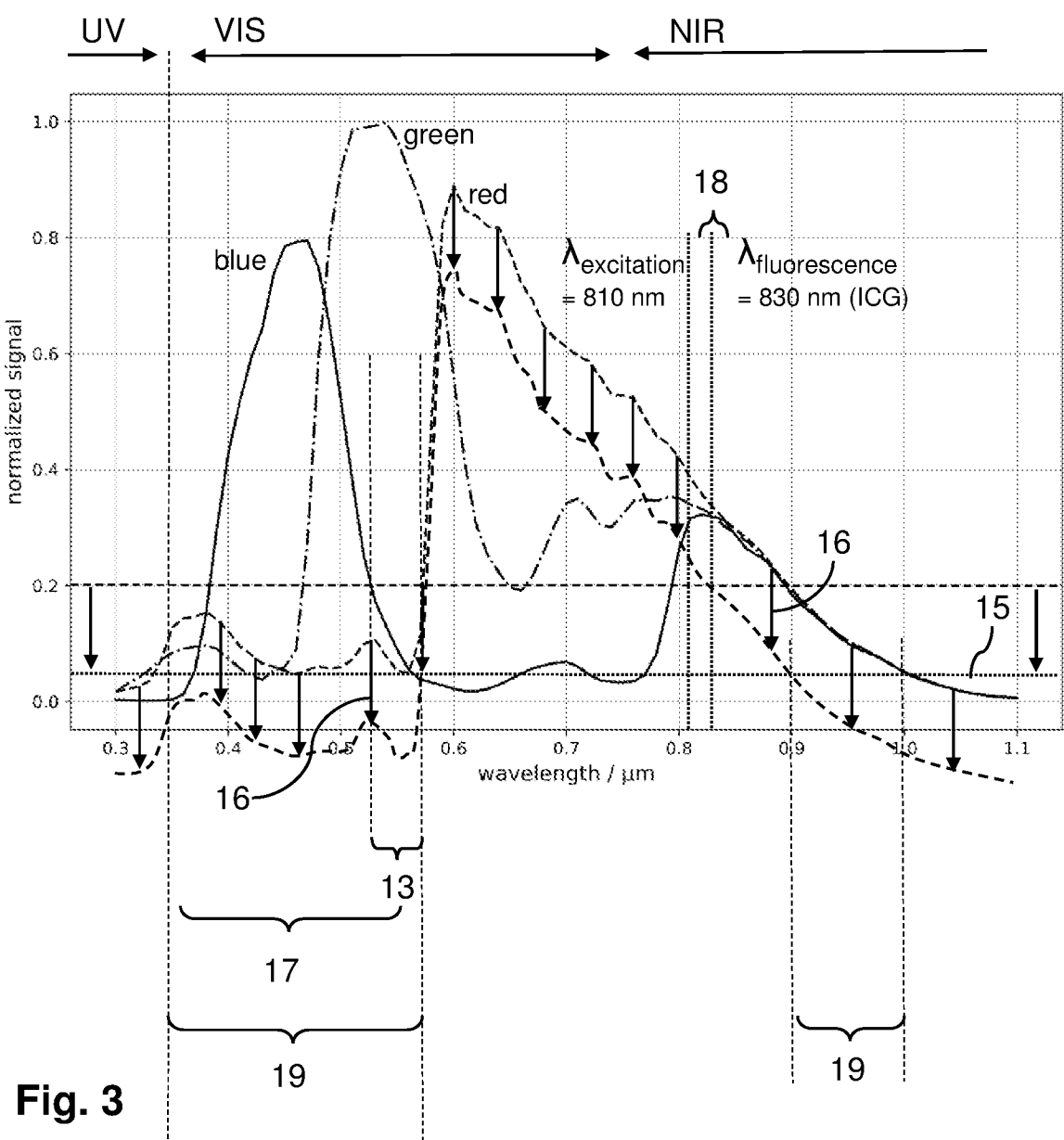
FIG. 3 shows a schematic representation of the sensitivities of individual color channels of the image sensor of the endoscopy system shown in FIG. 1, for the purposes of illustrating the imaging method according to the invention.

To achieve this object precisely without complex and computationally intensive signal processing, it is proposed to separate the signals of the individual color channels from one another by targeted selective reduction in the sensitivity of one of the color channels of the image sensor 7 (cf. the reduction 16 in FIG. 3). This is vividly illustrated in FIG. 3 which shows spectral sensitivity curves of the three color channels of the image sensor 7, said figure in exemplary fashion rendering an imaging method according to the invention understandable: In this case, the blue color channel of the image sensor 7 (solid line), referred to as main color channel below, is intended to be able to be separated from the red color channel (dashed line). Further, together with the further green color channel (dash-dotted line), the main color channel should be used for imaging in the visible (VIS) wavelength range while the red color channel is intended to record the fluorescence wavelength of 830 nm in the near infrared (NIR) range.

The sensitivity of the red color channel, which is referred to as "reduced color channel" below, is in this case reduced to the same extent for all detectable wavelengths, as indicated in FIG. 3 by the arrows pointing perpendicularly downward. In the example of FIG. 3, this is achieved by virtue of carrying out a global adaptation (i.e., an adaptation spectrally effective for all wavelengths) of the threshold correction of the red/reduced color channel. The dashed line of the red color channel accordingly shifts (or at least is imagined to shift) downward such that this color channel becomes "blind" in particular to wavelengths below approximately 550 nm and above approximately 900 nm.

To illustrate this, an omnispectral sensitivity threshold 15 (that is to say, an equal sensitivity threshold for all wavelengths) is plotted as a dotted horizontal line in FIG. 3. Since the depicted curves can also be understood to be luminous intensity curves, it is accordingly necessary for a certain intensity limit (for light at a certain wavelength) to be exceeded so that the image sensor 7 can recognize this light as such and can consequently detect this light. Below this intensity limit (which is proportional to the aforementioned sensitivity threshold), the signal produced by the respective wavelength is lost in the noise and is no longer recognized as a measurement signal, or the produced signal has no substantial component any more. In such a case, the affected light signal still is consequently captured by the sensor; however, if the spectral sensitivity value of the affected color channel is below the omnispectral sensitivity threshold, the light signal at the affected wavelength, which is in any case below the intensity limit, can no longer be detected using this color channel.

Before the sensitivity of the red color channel was reduced, all three color channels could still detect for example a luminous intensity amounting to the intensity threshold at a wavelength of 550 nm since all three curves were above the omnispectral sensitivity threshold 15 around here; by contrast, following the reduction of the red color channel, its sensitivity for wavelengths below approximately 575 nm is below the omnispectral sensitivity threshold 15, and so the red color channel still captures illumination light 10 in this wavelength range but is unable to measure the latter any more, or the signal component of the red color channel produced by the illumination light 10 is no longer substantial. These observations apply to the case where the illumination light intensity is below a global intensity limit. A corresponding restriction of the illumination light intensity below the intensity threshold can be implemented manually for example, or else by way of an automated control mechanism.

As further illustrated in FIG. 3, a fluorescent dye 9 (as already described above in relation to FIG. 1), specifically indocyanine green (ICG), is excited by means of excitation light 11 at a wavelength of 810 nm to emit fluorescence light 12. Both the illumination light 10 and the fluorescence light 12 is now captured by means of the image sensor 7 embodied as an individual chip. In the process, the excitation light 11 is kept away from the image sensor 7 with the aid of an optical filter which realizes a narrow bandwidth band-stop filter around 810 nm so that said high intensity light does not impede with the imaging of the red color channel in particular.

If the illumination light is now restricted to wavelengths below 550 nm (for instance to the first spectral range 17 illustrated in FIG. 3)—for instance by using further optical filters or by using appropriate light sources—this illumination light 10 from this first spectral range 17 is only measured by the blue main color channel and the green further color channel; by contrast, the red color channel is no longer able to measure light in this first spectral range (below a certain intensity threshold) on account of the implemented threshold adaptation since the red color channel is no longer sensitive in the visible spectrum to spectral signal components (below the intensity limit) below the limit wavelength 20 of 550 nm.

However, since the red color channel following the reduction 16 still also has a sufficient sensitivity around the fluorescence wavelength of 830 nm, the fluorescence light 12 can be measured using this reduced color channel. Accordingly, the red reduced color channel in this case spectrally selectively measures the fluorescence light 12 in the second spectral range 18 illustrated in FIG. 3, which lies outside of the first spectral range 17 of the illumination light 10 in the NIR. A spectral signal separation by means of computationally intensive and hence energy intensive signal processing is not required to this end. The only (acceptable) drawback consists of the fact that the dynamic range of the red color channel has been reduced as a result of the reduction 16. However, this can be compensated for by virtue of the fact that following the recording of the fluorescence light image component with the red reduced color channel, the latter's dynamic range is subsequently adjusted to an original dynamic range.

Therefore, a fluorescence light image component (FLBK), used to visualize the recorded fluorescence light 12, can also be calculated from the measurement signals of the reduced red color channel. By contrast, if a plurality of color channels of the image sensor 7 are reduced in terms of their respective sensitivity, for instance—in addition to the red color channel—a further color channel formed by IR pixels of the image sensor 7, these pixels may also contribute to the determination of the FLBK. In this case, the respective reduced color channels can also be reduced 16 to different extents, depending on the profile of the respective sensitivity curve.

In this case, the remaining imaging is not impeded by the fact that the blue and green color channel also continue to capture the fluorescence light 12 (and measure the latter—since the solid line of the blue color channel and the dash-dotted line of the green color channel are also still above the sensitivity threshold 15 at 830 nm); this is because the intensity of the fluorescence light 12 is very low in comparison with the intensity of the illumination light 10. Thus, while the red reduced color channel is used for fluorescence light imaging in this case, the blue main color channel and the further green color channel (which has not been reduced in terms of its sensitivity) can be used at the same time for VIS imaging in the visible wavelength range. There can also be a subsequent separation by subtracting the red signal since the latter has a virtually similar spectral sensitivity in all color channels in the wavelength range depicted here.

As already explained, there are numerous technical options for realizing a reduction 16 as proposed here:

a) By way of example, a threshold correction can be increased in the color channel to be reduced; in particular, this can be implemented by virtue of what is known as a black level, which is usually subtracted from the raw image data as a signal threshold, being increased. By way of example, the reduction 16 can be designed such that the threshold correction or black level correction of the red color channel is significantly higher than that of the blue and/or green color channel.

b) It is possible to adapt an electronic exposure time, in particular pixel-by-pixel;

c) It is possible to adapt a respective optical exposure time.

All such measures can lead to the color channel to be reduced being made insensitive (in any case for intensity values below a limit) in the first spectral range 17 used for the illumination.

Further, it was already described above that the individual color channels in this case can also be read at different times. In particular, this can be realized by means of a reduction function Reduce(t,x,y), which changes the reduction 16 of the respective color channel over a sensor surface A(x,y) of the image sensor 7 and/or as a function of time t.

What can be further identified on the basis of FIG. 3 is that the red and the blue color channel—in relation to the respective sensitivity—exhibited a spectral overlap range 13 prior to the reduction, for instance in the range of 550-575 nm, in which the respective sensitivities were above the sensitivity threshold 15. Consequently, prior to the reduction 16, spectral signal components (which were above the associated omnispectral intensity limit) in this overlap range 13 (which identifiably lies within the visible spectrum (VIS)) were still measurable with the main color channel and the reduced color channel.

By contrast, following the reduction 16 (cf. the lower dashed curve of the red color channel), the situation is such that the sensitivity of the red reduced color channel is below the omnispectral sensitivity threshold 15 in a (first) spectral separation range 19 of 350-575 nm. Therefore, the red reduced color channel is no longer able to measure light from the first spectral range 17 of the illumination light (below the omnispectral intensity limit). The same would also apply to the further separation range 19 of 900-1000 nm since the sensitivity of the reduced red color channel is also below the sensitivity threshold 15 there, while light (below the omnispectral intensity threshold) would still be measurable there using the blue and green color channel (even if no illumination light is used in this range any more).

In this case, what is decisive for the successful detection of the fluorescence light 12 is that the red color channel still is sensitive to spectral signal components (above the intensity limit) in the second spectral range 18, which is depicted in FIG. 3 and which comprises the fluorescence wavelength of 830 nm, even after the implemented reduction 16. As a result, this second spectral range 18 can be captured selectively using the red color channel and can be used for fluorescence imaging.

Since the reduction 16 can be activated and deactivated, the red color channel can also be used—as is customary—in a second imaging mode together with the red and blue color channel, initially without a reduction 16, as a non-reduced main color channel for imaging in the visible wavelength range. In this mode a surgeon can consequently exploit the full capability of the image sensor 7, for example in order to inspect an operation site in detail and in full color. By way of example, there can be a switch into a first imaging mode after pathological tissue has been found, the red color channel being used as a reduced color channel—as described above—for fluorescence light imaging in said first imaging mode, for instance in order to make details of the pathological tissue visible by means of fluorescent markers.

It is understood that the illumination light 10 can also be adapted in the individual imaging modes: Thus, the illumination light 10 may also contain visible (e.g., red) wavelengths in the second imaging mode, said wavelengths also being detected by the then non-reduced red color channel. These wavelengths are then deactivated in the first imaging mode, or are masked by means of filters, such that the desired restriction of the illumination light 10 to a first wavelength range 17 is implemented (for instance, as illustrated in FIG. 3), said wavelength range no longer being able to be detected with the then reduced color channel. Consequently, the first imaging mode may be accompanied by a certain restriction of the illumination light 10 in comparison with the second imaging mode; nevertheless, the surgeon can continue to use the image sensor 7 in the visible wavelength range for imaging even in the first imaging mode, specifically using the green and blue color channel, with which the first wavelength range 17 can then also still be detected.

Expressed differently, one and the same color channel (the red color channel in the example of FIG. 3) can accordingly be used in a second imaging mode using white-light illumination and in a first imaging mode as a reduced color channel with an illumination restricted to the first spectral range 17.

In the case of such imaging with a restricted illumination in the visible range, it is consequently possible to capture a first polychromatic image component using the blue and green color channel (VIS image component) and moreover possible to capture a further monochromatic image component with the red reduced color channel (fluorescence light image components—FLBK). By contrast, if two reduced color channels are used—for instance, a reduced red color channel and a reduced IR color channel—then even this second image component can likewise be polychromatic. In particular, this may lend itself to the case where a plurality of fluorescent dyes with different fluorescence wavelengths are used.

The method according to the invention can be even further refined by virtue of the reduction 16 still being implemented spectrally globally but the magnitude of said reduction depending on the respective position of the pixel, that is to say this is implemented pixel-by-pixel, i.e., with spatial resolution. This can not only achieve that the reduction of the sensitivity of the red color channel is implemented independently of an employed sensitivity of the blue or green color channel for instance, but it is also possible for instance to take account of current intensity measurement values of pixels. As a result, the sensitivity of the reduced color channel can be exploited to the full.

In summary, for the simplified, in particular less computationally intensive, image recording of different spectral signal components using a plurality of color channels of a single image sensor 7, a targeted adjustment, in particular a relative increase or reduction 16, of a sensitivity of at least one of the color channels in relation to at least one sensitivity of another one of the color channels of the image sensor 7 is proposed for a spectral separation of this reduced or adjusted color channel from the other color channel. As a result, at least one certain spectral range 19, in particular a part of a first spectral range 17 captured using the other color channel, can be no longer detectable using the color channel that has been adjusted in terms of its sensitivity. What can be achieved accordingly is that this adjusted, in particular reduced, color channel becomes spectrally blind in said spectral range 19 and can consequently spectrally selectively detect a further spectral range 18 (in particular a second spectral range deviating from the first spectral range). In this case, this second spectral range 18 may in particular comprise a fluorescence wavelength.

LIST OF REFERENCE SIGNS

1 Endoscopy system
2 Endoscope
3 Light source for illumination light
4 Camera control unit (CCU)
5 Monitor
6 Cable
7 Image sensor
8 Tissue (observed by 2/7)
9 Fluorescent dye
10 Illumination light
11 Excitation light
12 Fluorescence light
13 Spectral overlap range
14 Shaft (of 2)
15 Omnispectral sensitivity threshold
16 Reduction (of the reduced color channel)

17 First spectral range (for imaging using the main channel of 7)

18 Second spectral range

19 Spectral separation range

20 Limit wavelength

The invention claimed is:

1. An imaging method, comprising:

illuminating a scene by an illumination light (10) in a first spectral range (17);

recording the illumination light (10) by a main color channel of an image sensor (7);

providing the image sensor (7) with at least one further color channel; and selectively and actively reducing a sensitivity of the at least one further color channel in comparison with a sensitivity of the main color channel to provide at least one reduced color channel such that after activation of the reducing of the sensitivity of the at least one reduced color channel the illumination light (10) in the first spectral range (17) is still captured by the reduced color channel but produces only a negligibly small signal component, as compared to before the activation of the reducing of the sensitivity of the reduced color channel, wherein the reduction of the sensitivity of the at least one reduced color channel is configured to be activated and deactivated, such that the at least one reduced color channel is also useable without said reduction as a non-reduced main color channel for imaging in the visible wavelength range.

2. The imaging method as claimed in claim 1, further comprising:

exciting at least one fluorescent dye (9) via an excitation light (11) to emit fluorescence light (12), and measuring and recording both the illumination light (10) and the fluorescence light (12) using the image sensor (7); and at least one of (a) the fluorescence light (12) is measured using the at least one reduced color channel, or (b) the at least one reduced color channel is used for imaging the fluorescence light and the main color channel is used for imaging VIS in a visible wavelength range at a same time.

3. The imaging method as claimed in claim 1, wherein at least one of (a) prior to the sensitivity reduction, respective spectral sensitivities of the main color channel and of the reduced color channel overlap in at least one spectral overlap range (13), in which the respective sensitivities are above an omnispectral sensitivity threshold (15), or (b) following the reduction in the sensitivity of the reduced color channel, the reduced sensitivity of the reduced color channel in at least one spectral separation range (19) lies below the omnispectral sensitivity threshold (15).

4. The imaging method as claimed in claim 3, wherein the at least one overlap range (13) lies within a first spectral range (17) of the visible spectrum, and the at least one reduced color channel following the sensitivity reduction remains sensitive to spectral signal components above the intensity threshold in a second spectral range (18) lying outside of the first spectral range (17).

5. The imaging method as claimed in claim 1, further comprising:

reducing a dynamic range of the at least one reduced color channel by the sensitivity reduction in comparison with at least one of a dynamic range prior to the sensitivity reduction or a dynamic range of the main color channel.

6. The imaging method as claimed in claim 1, wherein the sensitivity of the at least one reduced color channel in a first imaging mode, in which the at least one reduced color channel is used for the fluorescence light imaging, is reduced in comparison with a sensitivity in a second imaging mode, in which the reduced color channel is used as a non-reduced main color channel for imaging in the visible wavelength range.

7. The imaging method as claimed in claim 1, wherein the reduction in the sensitivity of the at least one reduced color channel is implemented pixel-by-pixel such that only pixels of the image sensor (7) which belong to the at least one reduced color channel are used for measuring fluorescence light.

8. The imaging method as claimed in claim 1, further comprising:

calculating or deriving a fluorescence light image component (FLBK) used to visualize recorded fluorescence light exclusively from output signals of the at least one reduced color channel.

9. The imaging method as claimed in claim 1, wherein the sensitivity of the at least one reduced color channel is reduced by virtue of, for the at least one reduced color channel, at least one of:

A) a threshold correction being increased,

B) an electronic exposure time being at least one of continuously or alternately reduced in comparison with an electronic exposure time used for the main color channel, or C) wherein the individual color channels of the image sensor (7) are read sequentially and an optical exposure time is adapted at least one of continuously or alternately such that the at least one reduced color channel is optically exposed for a shorter time period than the main color channel.

10. The imaging method as claimed in claim 1, wherein the sensitivity of the at least one reduced color channel and a sensitivity of the main color channel are reduced and increased dynamically, and the at least one reduced color channel and the main color channel are read at different times.

11. The imaging method as claimed in claim 1, wherein a sensitivity of individual pixels of the at least one reduced color channel is reduced at least one of (a) differently pixel-by-pixel, or (b) to a different extent at different image recording times.

12. The imaging method as claimed in claim 1, wherein the sensitivity reduction is implemented with at least one of:

(a) a local variation in relation to a sensor surface of the image sensor (7), or (b) a time variation in relation to different exposure times of individual pixels of the image sensor (7).

13. The imaging method as claimed in claim 1, wherein the main color channel is used to record a first image component in a first spectral range of the visible spectrum, the at least one reduced color channel is used simultaneously to record a second image component in a second spectral range (18), in particular the second spectral range, which lies outside of the first spectral range (17), and the second image component is one of (a) a monochromatic image component recorded using a reduced color channel, or (b) a polychromatic image component which is determined using at least two reduced color channels.

14. The imaging method as claimed in claim 1, wherein the image sensor (7) is usable or used in a second imaging mode, in which imaging is carried out in the visible wavelength range (VIS), using one of the color channels of the image sensor (7) which is used in a first imaging mode.

15. The imaging method as claimed in claim 1, wherein the sensitivity of the at least one reduced color channel is reduced pixel-by-pixel for individual pixels of the image sensor (7) based on a current intensity measurement value of a respective pixel.

16. The imaging method as claimed in claim 1, wherein the reduction in the sensitivity of the at least one reduced color channel is implemented based on at least one of:

an illumination light intensity currently used for imaging,
a current operation or imaging mode,
a current electronic gain or analog gain,
a utilized exposure time,
a currently used system component comprising a light source, or
at least one secondary parameter, including one of
values of a color matrix used to adjust a color representation, or
values of a false color or heat map representation of images recorded using the method.

17. The imaging method as claimed in claim 1, further comprising:

recording raw image data using at least the main color channel and the at least one further color channel of the image sensor (7);
subtracting a signal threshold from the raw image data in each case, wherein
a first set of signal thresholds is used in a first mode, and
a second set of signal thresholds is used in a second mode, to correct the respectively recorded raw image data, with at least one of a difference or a quotient of the signal thresholds of the first set being different from at least one of a difference or a quotient of the signal thresholds of the second set.

18. The imaging method as claimed in claim 17, further comprising:

illuminating the scene by the illumination light (10) for an image recording, and
applying a threshold correction to the reduced color channel of the at least two color channels that is greater than a threshold correction applied to the main color channel of the image sensor.

19. An endoscopy system (1), comprising:

an image sensor (7) embodied as an individual chip which has at least two color channels that are formed by a color filter array (CFA), including a main color channel and at least one further color channel;

a light source configured for producing illumination light (10) within a first spectral range (17) of the visible spectrum (VIS) and excitation light (11) for exciting an emission of fluorescence light (12) lying in a second spectral range (18) outside of the first spectral range (17);

an image processing unit (4) configured to selectively and actively reduce a sensitivity of said at least one further color channel in relation to a sensitivity of the main color channel, such that after activation of the reduction of the sensitivity the at least one further color channel forms a reduced color channel, the illumination light (10) in the first spectral range (17) is still captured by the reduced color channel but produces only a negligibly small signal component, as compared to before the activation of the reduction of the sensitivity of the reduced color channel;
capture the fluorescence light (12) using at least one reduced color channel of the color channels of the image sensor (7); and
record the illumination light (10) by the at least one main color channel,
wherein the reduction of the sensitivity of the at least one reduced color channel is configured to be activated and deactivated, such that the at least one reduced color channel is also useable without said reduction as a non-reduced main color channel for imaging in the visible wavelength range.

20. The endoscopy system (1) as claimed in claim 19, wherein the image processing unit (4) is configured to implement an imaging method including illuminating a scene by the illumination light (10) in the first spectral range (17);
recording the illumination light (10) by the main color channel of the image sensor (7); and
selectively and actively reducing the sensitivity of the at least one further color channel in comparison with the sensitivity of the main color channel to provide the at least one reduced color channel such that the illumination light (10) in the first spectral range (17) is still captured by the reduced color channel but produces only a negligibly small signal component, as compared to before the activation of the reduction of the sensitivity of the reduced color channel.

* * * * *